US007645434B2

(12) United States Patent
Welz-Biermann et al.

(10) Patent No.: US 7,645,434 B2
(45) Date of Patent: Jan. 12, 2010

(54) SALTS COMPRISING CYANOBORATE ANIONS

(75) Inventors: Urs Welz-Biermann, Heppenheim (DE); Nikolai (Mykola) Ignatyev, Duisburg (DE); Eduard Bernhardt, Duisburg (DE); Maik Finze, Nienburg (DE); Helge Willner, Mühlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 712 days.

(21) Appl. No.: 10/545,690

(22) PCT Filed: Jan. 15, 2004

(86) PCT No.: PCT/EP2004/000231

§ 371 (c)(1),
(2), (4) Date: Aug. 15, 2005

(87) PCT Pub. No.: WO2004/072089

PCT Pub. Date: Aug. 26, 2004

(65) Prior Publication Data

US 2006/0222584 A1 Oct. 5, 2006

(30) Foreign Application Priority Data

Feb. 14, 2003 (DE) ................. 103 06 617

(51) Int. Cl.
 *C01C 3/11* (2006.01)
(52) U.S. Cl. ...................... 423/377; 423/276
(58) Field of Classification Search ............. 423/377
 See application file for complete search history.

(56) References Cited

U.S. PATENT DOCUMENTS 4,892,944 A 1/1990 Mori et al.

6,815,119 B2 11/2004 Schmitt et al.
2004/0002002 A1 1/2004 Mizuta et al.

FOREIGN PATENT DOCUMENTS

| JP | 63284148 A2 | 11/1998 |
| JP | 2002308884 A | 10/2002 |
| JP | 2004165131 A2 | 6/2004 |
| JP | 2004175666 A2 | 6/2004 |

OTHER PUBLICATIONS

Bernhadt et. al. Chem. Eur. J. 2001, 7, No. 21, 4696-4705.*
Bernhardt et al., Z. Anorg. Allg. Chem. 2000, 626, 560-568.*
Bernhardt, E. et al: "The Tetracyanoborates M[B(CN)4], M-[Bu4n]+, Ag+, K+"Zeitschrift Fuer Anorganische Und Allgemeine Chemie, 626(2), 560-568 Coden: Zaacab; ISSN: 0044-2313, 2000, xp0009030010.
Holbrey J et al, "The phase behaviour of 1-alkyl-3-methylimidazolium tetrafluoroborates; ionic liquids and ionic liquid crystals", J. Chem. Soc. Dalton Trans., 1999, pp. 2133-2139.
Williams, Darrick et al: Synthesis of LIBC4N4, BC3N3, and Related C-N Compounds of Boron: New Precursors Tolight Element Ceramics: Journal of the American Chemical Society, 122 (32), 7735-7741 Coden: Jacsat; ISSN: 0002-7863, 2000, XP002278152.
Bernhardt, E. et al: "The Tetracyanoborates M[B(CN)4], M-[Bu4n]+, Ag+, K+"Zeitschrift Fuer Anorganische Und Allgemeine Chemie, 626(2), 560-568 Coden: Zaacab; ISSN: 0044-2313, 2000, xp0009030010.
Bernhardt, E. et al: "An Efficient Synthesis for Tetracyanoborates by Sinter Processes" Zeitschrift Fuer Anorganische Und Allgemeine Chemie, 629(7-8), 1229-1234 Coden: Zaacab; ISSN: 0044-2313, 2003, XP0009030008.

* cited by examiner

*Primary Examiner*—Roy King
*Assistant Examiner*—Yun Qian
(74) *Attorney, Agent, or Firm*—Millen, White, Zelano & Branigan, P.C.

(57) ABSTRACT

A process for the preparation of alkali metal cyanoborates, the further conversion thereof into salts comprising cyanoborate anions and organic cations, these salts, and the use thereof as ionic liquids are described.

23 Claims, No Drawings

SALTS COMPRISING CYANOBORATE ANIONS

The present invention relates to a process for the preparation of alkali metal cyanoborates, to the further conversion thereof into salts comprising cyanoborate anions and organic cations, to these salts, and to the use thereof as ionic liquids.

Ionic liquids or liquid salts are ionic species which consist of an organic cation and a generally inorganic anion. They do not contain neutral molecules, and generally have melting points below 373 K. A multiplicity of compounds which are used as ionic liquids are known in the prior art. In particular, they are also the subject-matter of a series of patents and patent applications.

Thus, solvent-free ionic liquids were disclosed for the first time by Hurley and Wier in a series of US patents (U.S. Pat. Nos. 2,446,331, 2,446,339 and 2,446,350). These "salts which are molten at room temperature" comprised $AlCl_3$ and a multiplicity of n-alkylpyridinium halides.

In recent years, some review articles have been published on this topic (R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083; R. Hagiwara, Ya. Ito "Room temperature ionic liquids of alkylimidazolium cations and fluoroanions", *Journal of Fluorine Chem.*, 105 (2000), 221-227).

The properties of ionic liquids, for example melting point, thermal and electrochemical stability, viscosity, are greatly influenced by the nature of the anion. By contrast, the polarity and hydrophilicity or lipophilicity can be varied through a suitable choice of the cation/anion pair. There is therefore a basic demand for novel ionic liquids having varied properties which facilitate additional possibilities with respect to their use.

Crucial advances in the area of ionic liquids have been achieved with the discovery of 1-ethyl-3-methylimidazolium chloroaluminate. This salt has a broad liquid range and an electrochemical window of greater than 3 V and is thus of great interest for electrochemical and synthetic purposes. However, its use is limited by the chemical instability, especially to moisture. After the discovery of the more hydrolysis-stable 1-ethyl-3-methylimidazolium tetrafluoroborate, combinations of alkylimidazolium cations with inorganic or organic anions were investigated, of which 1-ethyl-3-methylimidazolium tetrafluoroborate is the best characterised.

The stability of the imidazolium cation is relatively high and its decomposition temperature is essentially determined by the anion. Thus, 1-ethyl-3-methylimidazolium salts with triflate and bis(trifluoromethylsulfonyl)imide anions are stable up to 400° C., whereas 1-ethyl-3-methylimidazolium tetrafluoroborate is only stable up to 300° C.

The prior art describes borate anions in which fluorine ligands have been replaced by cyanide (E. Bernhardt, G. Henkel, H. Willner, *Z. Anorg. Allg. Chem.* 626 (2000) 560; D. Williams, B. Pleune, J. Kouvetakis, M. D. Williams, R. A. Andersen, *J. Amer. Chem. Soc.* 122 (2000) 7735; E. Bernhardt, M. Berkei, M. Schürmann, H. Willner, *Z. Anorg. Allg. Chem.* 628 (2002) 1734) and trifluoromethyl ligands (E. Bernhardt, G. Henkel, H. Willner, G. Pawelke, H. Bürger, *Chem. Eur. J.* 7 (2001) 4696; G. Pawelke, H. Bürger, *Coord. Chem. Rev.* 215 (2001) 243). The trifluoromethyl borates are synthesised here starting from the cyanoborates, but the cyanoborates are only accessible with difficulty and in small amounts. The synthesis of $[B(CN)_4]^-$ is labour-intensive and can only be carried out on a small preparative scale. In addition, the starting materials are expensive.

The object of the present invention is to provide novel stable compounds having valuable properties which can be used as ionic liquids, and a process for the preparation thereof. In particular, the object is to provide salts with borate anions which have higher stability than the salts with tetrafluoroborate anions.

A further object of the present invention is to provide an effective and economical process for the preparation of these borate salts and their precursors.

This object is achieved in accordance with the invention by the characterising features of the main claim and the subclaims.

The present invention therefore relates firstly to a process for the preparation of alkali metal cyanoborates of the general formula (1)

$$M^+[B(CN)_4]^- \qquad (1),$$

where M is selected from the group Li, Na, K, Rb and Cs, in which the readily available starting substances alkali metal tetrafluoroborate $M[BF_4]$ (M=Li, Na, K, Rb, Cs) and alkali metal cyanide MCN (M=Li, Na, K, Rb, Cs) are reacted with one another in a solid-state reaction.

The alkali metal tetrafluoroborate used in accordance with the invention is preferably potassium tetrafluoroborate $K[BF_4]$ or sodium tetrafluoroborate $Na[BF_4]$, and the alkali metal cyanide used in accordance with the invention is preferably potassium cyanide KCN or sodium cyanide NaCN.

In a preferred variant of the process according to the invention, the alkali metal tetrafluoroborate is reacted with the alkali metal cyanide in the presence of a lithium halide. The lithium halide here is selected from LiCl, LiBr and LiI, it is particularly preferably lithium chloride LiCl.

Alkali metal cyanide and lithium halide can in each case be employed in an excess of one of the two reagents. However, the alkali metal cyanide and the lithium halide are preferably brought to reaction in approximately in the molar ratio 1:1.

The alkali metal tetrafluoroborate and the alkali metal cyanide are preferably employed in the molar ratio of 1:4 to 1:12, particularly preferably in the molar ratio of about 1:9.

The alkali metal tetrafluoroborate:alkali metal cyanide:lithium halide molar ratio of about 1:9:9 is therefore very particularly preferably used.

The starting materials used for the reaction according to the invention are particularly preferably potassium tetrafluoroborate $K[BF_4]$ as alkali metal tetrafluoroborate and potassium cyanide KCN as alkali metal cyanide.

The solid-state reaction according to the invention is carried out at temperatures between 100° C. and 500° C. Preference is given to temperatures of 250 to 400° C., particularly preferably 280-340° C.

Without restricting generality, the subject-matter of the solid-state reaction according to the invention is explained with reference to a general example: $K[BF_4]$, KCN and LiCl are mixed in the molar ratio of 1:9:9 and subsequently brought to reaction in the melt. The reaction temperature is selected in such a way that on the one hand the KCN/LiCl mixture forms a eutectic melting at 270-290° C. and on the other hand the tetracyanoborate salts formed only decompose slowly (<400-500° C.). Evaluation of powder diffractograms of the cooled melt of KCN with LiCl (molar ratio 1:1) enables mixed crystals of the K(Cl,CN) type (a=6.34 Å, F m3m) and a further unidentified compound (d=4.958, 2.878, 2.728, 2.482, 2.175 Å) to be detected. The yield of K[B(CN)$_4$] is virtually temperature-independent in the range 280-340° C. and is about 40-60%, based on K[BF$_4$]. It is found in further experiments that a reduction in the molar ratio of K[BF$_4$] to KCN/LiCl from 1:9 to 1:4.5 results in reductions in yield. The Raman spectra of the reaction mixtures show that the tetracyanoborate is in the form of the lithium salt after the reaction (v(CN)=2263 cm$^{-1}$).

In the analogous reaction using an NaCN/LiCl mixture, mixed crystals of the (Li,Na)(Cl,CN) type (a=5.50 Å Fm3m) form in the melt of NaCN with LiCl (molar ratio 1:1) besides a little LiCN (d=5.216, 3.626 Å, m.p. 160° C.). A eutectic (120-140° C.) forms between NaCN with LiCl, in contrast to KCN/LiCl, but the mixed crystals only melt at 360-540° C.; this is probably the cause of the lower yields (about 25%) of Na[B(CN)$_4$].

During work-up of the reaction products, the excess cyanide must firstly be destroyed. It is found that oxidation of the cyanide using aqueous 30% H$_2$O$_2$ solution is the best work-up method. The low salt burden and the complete and rapid degradation of the cyanide remaining in the reaction mixture, as well as the good yields outweigh the single disadvantage, the often vigorous and difficult-to-control reaction of the cyanide. The tetracyanoborate is subsequently extracted from the aqueous solution and converted into the K or Na salt by re-extraction.

An alternative method available for the work-up of the solid-state reaction products is oxidation of the unreacted cyanide using aqueous NaOCl solution, which proceeds within a few minutes under very mild conditions, i.e. without warming or foaming of the reaction mixture. The work-up is then carried out analogously to that with H$_2$O$_2$. However, this further work-up is more labour-intensive and time-consuming owing to the greater salt burden.

The present invention furthermore relates to a process for the preparation of alkali metal cyanoborates of the general formula (2)

$$M^+[BF_n(CN)_{4-n}]^- \qquad (2),$$

where n=0, 1, 2 or 3 and

M is selected from the group Li, Na, K, Rb and Cs, in which an alkali metal cyanide MCN, where M=Li, Na, K, Rb, Cs, is reacted with boron trifluoride etherate BF$_3$·OEt$_2$.

On use of coarse-grained potassium cyanide KCN and BF$_3$·OEt$_2$, equimolar amounts of K[BF$_4$] and K[BF$_2$(CN)$_2$] also form in the reaction according to the invention alongside the primary adduct K[BF$_3$(CN)], in accordance with the following equations:

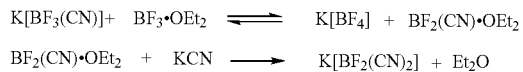

In addition, the two salts K[BF(CN)$_3$] and K[B(CN)$_4$] form to a lesser extent, the former in particular if the reaction mixture is held at temperatures above room temperature.

In accordance with the invention, the boron trifluoride etherate is reacted with the alkali metal cyanide in the presence of an aprotic solvent. Without restricting generality, the aprotic solvent can be, for example, acetonitrile, diethyl ether, tetra-hydrofuran and/or dimethoxyethane.

The alkali metal cyanide used for the process according to the invention is preferably potassium cyanide KCN.

The starting materials are preferably reacted in accordance with the invention at temperatures of −80 to 100° C., particularly preferably at room temperature.

Volatile by-products which are removed under reduced pressure may be formed during the reaction. Mostly, however, by-products which are insoluble in the solvents used and are separated off by filtration form. The solvent is, if desired, removed under reduced pressure together with volatile by-products, and the alkali metal cyanoborates obtained can, if desired, be separated and purified by a common possibility known to the person skilled in the art.

A third and fourth subject-matter of the present invention are a process for the preparation of salts with cyanoborate anions of the general formula (3) and the corresponding salts of the general formula (3)

$$Kt^+[BF_n(CN)_{4-n}]^- \qquad (3),$$

where n=0, 1, 2 or 3, and Kt$^+$ is an organic cation, with the proviso that the cation Kt$^+$ is not [N(C$_4$H$_9$)$_4$]$^+$ for n=0.

For the preparation of the salts, an alkali metal cyanoborate of the general formula M$^+$[B(CN)$_4$]$^-$, where M is selected from the group Li, Na, K, Rb and Cs, or an alkali metal cyanoborate of the general formula M$^+$[BF$_n$(CN)$_{4-n}$]$^-$, where n=0, 1, 2 or 3 and M is selected from the group Li, Na, K, Rb and Cs, is reacted with Kt$^+$X$^-$, where X is a halogen selected from Cl, Br and I, and Kt$^+$ is an organic cation, with the proviso that the cation Kt$^+$ is not [N(C$_4$H$_9$)$_4$]$^+$ for n=0.

The organic cation Kt$^+$ is preferably selected from the group

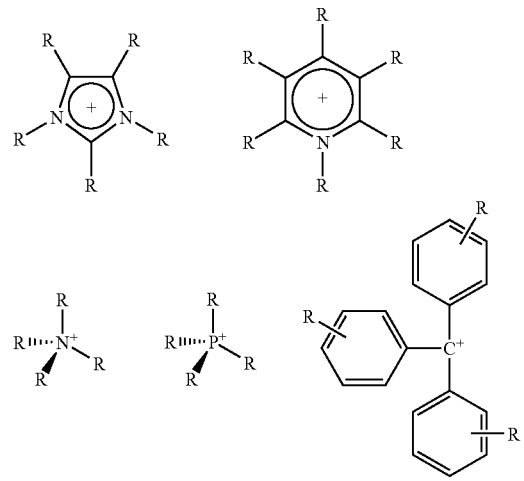

where R=H, with the proviso that at least one R on the hetero atom is different from H, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, in particular fluorine or chlorine, with the proviso that no halogen-hetero atom bond is present, —NO$_2$, with the proviso that no bond to a positively charged hetero atom is present, and at least one R is different from NO$_2$, —CN, with the proviso that no bond to a positively charged hetero atom is present, and at least one R is different from CN, where the R are in each case identical or different, where the R may be bonded to one another in pairs by single or double bond, where one or more R may be partially or fully substituted by halogens, in particular —F and/or —Cl, or partially by —CN or —NO$_2$, with the proviso that not all R are fully halogenated, and where one or two carbon atoms of the R may be replaced by hetero atoms and/or atom groups selected from the group —O—, —C(O)—, C(O)O—, —S—, —S(O)—, —SO$_2$—, —S(O)$_2$O—, —N=, —P=, —NR'—, —PR'—, —P(O)(OR')—, —P(O)(OR')O—, —P(O)(NR'R')—, —P(O)(NR'R')O—, —P(O)(NR'R')NR'—, —S(O)NR'— and —S(O)$_2$NR'—, where R'=H, non-, partially or perfluorinated C$_1$- to C$_6$-alkyl or non-, partially or perfluorinated phenyl.

For the purposes of the present invention, fully unsaturated substituents are also taken to mean aromatic substituents.

Besides hydrogen, suitable substituents R of the organic cation in accordance with the invention are: C$_1$- to C$_{20}$—, in particular C$_1$- to C$_{12}$-alkyl groups, C$_2$— to C$_{20}$—, in particular C$_2$— to C$_{12}$—, alkenyl or alkynyl groups, saturated or unsaturated, i.e. also aromatic, C$_3$- to C$_7$-cycloalkyl groups, NO$_2$, CN or halogens. However, a restricting factor for the halogens here is that they only occur as substituents on carbon atoms, but not on hetero atoms. NO$_2$ and CN do not occur as substituents of a positively charged hetero atom; furthermore, not all substituents simultaneously have the meaning of NO$_2$ or CN.

The substituents R may also be bonded in pairs in such a way that cyclic, bi- or polycyclic cations are formed. The substituents may be partially or fully substituted by halogen atoms, in particular by F and/or Cl, or partially by CN or NO$_2$ and contain one or two hetero atoms or atom groups, selected from the group 0, (O), C(O)O, S, S(O), SO$_2$, SO$_2$O, N, P, NH, PH, NR', PR', P(O)(OR'), P(O)(OR')O, P(O)(NR'R'), P(O)(NR'R')O, P(O)(NR'R')NR', S(O)NR' and S(O)$_2$NR'. In the case of complete halogenation, however, not all substituents R present may be fully halogenated, i.e. at least one R is not perhalogenated.

Without restricting generality, examples of substituents according to the invention of the organic cation are:

—F, —Cl, —Br, —I, —CH$_3$, —C$_2$H$_5$, —C$_3$H$_7$, —CH(CH$_3$)$_2$, —C$_4$H$_9$, —C(CH$_3$)$_3$, —C$_5$H$_{11}$, —C$_6$H$_{13}$, —C$_6$H$_{13}$, —C$_7$H$_{15}$, —C$_8$H$_{17}$, —C$_9$H$_{19}$, —C$_{10}$H$_{21}$, —C$_{12}$H$_{25}$, —C$_{20}$H$_{41}$, —OCH$_3$, —OCH(CH$_3$)$_2$, CH$_2$OCH$_3$, —C$_2$H$_4$OCH(CH$_3$)$_2$, —SCH$_3$, —SCH(CH$_3$)$_2$, —C$_2$H$_4$C$_2$H$_5$, —C$_2$H$_4$SCH(CH$_3$)$_2$, —S(O)CH$_3$, —SO$_2$CH$_3$, —SO$_2$C$_2$H$_5$, —SO$_2$C$_3$H$_7$, —SO$_2$CH(CH$_3$)$_2$, —CH$_2$SO$_2$CH$_3$, —OSO$_2$CH$_3$, —OSO$_2$CF$_3$, —CH$_2$N(H)C$_2$H$_5$, —C$_2$H$_4$N(H)C$_2$H$_5$, —CH$_2$N(CH$_3$)CH$_3$, —C$_2$H$_4$N(CH$_3$)CH$_3$, —N(CH$_3$)$_2$, —N(CH$_3$)C$_3$H$_5$, —N(CH$_3$)CF$_3$, O—C$_4$H$_8$—O—C$_4$H$_9$, —S—C$_2$H$_4$—N(C$_4$H$_9$)$_2$, —OCF$_3$, —S(O)CF$_3$, —SO$_2$CF$_3$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CF=CF$_2$, —C(CF$_3$)=CFCF$_3$, —CF$_2$CF=CFCF$_3$, —CF=CFN(CF$_3$)CF$_3$, —CFH$_2$, —CHF$_2$, —CH$_2$CF$_3$, —C$_2$F$_2$H$_3$, —C$_3$H$_6$, —CH$_2$C$_3$F$_7$, —C(CFH$_2$)$_3$, —CHO, —C(O)OH, —CH$_2$C(O)OH, —CH$_2$C(O)CH$_3$, —CH$_2$C(O)C$_2$H$_5$, —CH$_2$C(O)OCH$_3$, CH$_2$C(O)OC$_2$H$_5$, —C(O)CH$_3$, —C(O)OCH$_3$,

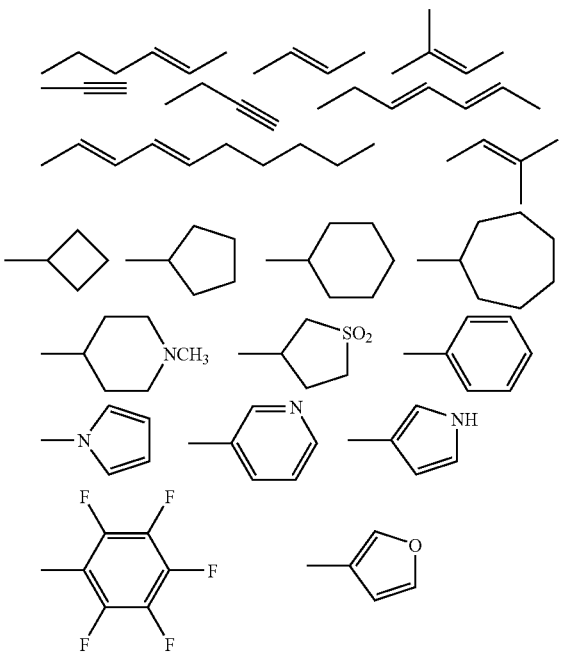

Without restricting generality, the following organic cations are particularly preferred as salts according to the invention:

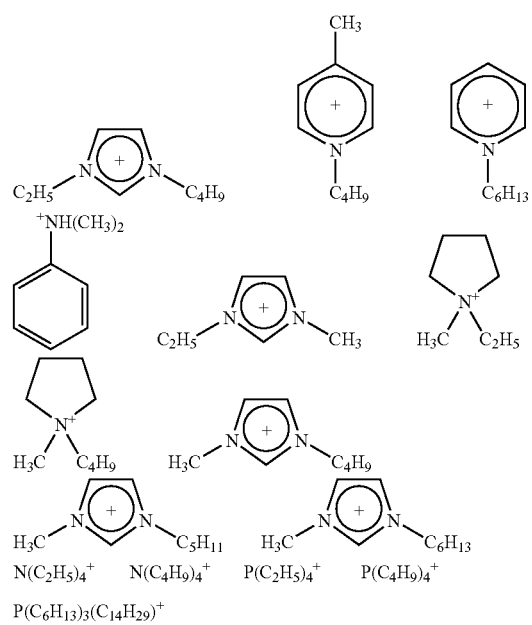

The salts according to the invention are advantageously very readily soluble in organic solvents. In comparison to known liquid salts, the salts according to the invention surprisingly have low viscosity. The salts according to the invention are advantageously stable. They can be isolated and stored at room temperature. Furthermore, the salts according to the invention are relatively easy to prepare, and readily available starting materials are required.

All compounds according to the invention and compounds of the formula [N(C$_4$H$_9$)$_4$]$^+$[B(CN)$_4$]$^-$ have a salt-like character, relatively low melting points (usually below 100° C.) and can be used as ionic liquids.

The salts according to the invention and salts of the formula $[N(C_4H_9)_4]^+[B(CN)_4]^-$ can be employed as solvents for many synthetic or catalytic reactions, for example Friedel-Crafts acylation and alkylation, Diels-Alder cycloadditions, hydrogenation and oxidation reactions, Heck reactions. Furthermore, for example, fluorinated solvents for secondary and primary batteries can be synthesised.

The salts according to the invention and salts of the formula $[N(C_4H_9)_4]^+[B(CN)_4]^-$ are suitable as precursors for the preparation of liquid-crystal compounds and of active ingredients, inter alia for medicaments and crop-protection agents.

It is also possible to use the compounds according to the invention and the salts of the formula $[N(C_4H_9)_4]^+[B(CN)_4]^-$ as non-aqueous electrolyte, optionally in combination with other electrolytes known to the person skilled in the art.

In addition, the salts according to the invention and salts of the formula $[N(C_4H_9)_4]^+[B(CN)_4]^-$ are of interest as non-aqueous, polar substances in suitable reactions as phase-transfer catalyst or as medium for the heterogenisation of homogeneous catalysts.

The complete disclosure content of all applications, patents and publications mentioned above and below are incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. in a Bruker Avance DRX-300 spectrometer with a 5 mm $^1$H/BB broad-band head with deuterium lock. The measurement frequencies of the various nuclei are: $^1$H: 300.13 MHz, $^{11}$B: 96.92 MHz, $^{13}$C, 75.47 MHz, $^{19}$F: 282.41 MHz and $^{15}$N: 30.41 MHz. The referencing method is indicated separately for each spectrum or each data set.

DSC measurements were carried out in a Netzsch DSC 204 instrument. The temperature and sensitivity were calibrated using naphthalene, benzoic acid, $KNO_3$, $AgNO_3$, $LiNO_3$ and CsCl. In each case, 5-20 mg of the substances were weighed out into an aluminium crucible and sealed with aluminium caps with a small aperture. The investigation was carried out in the temperature range from 25 to 500° C. Unless indicated otherwise, the heating rate is 10 Kmin$^{-1}$. During the measurement, the sample space was flushed with dry nitrogen. The samples of air-sensitive substances were prepared in a dry box and transported to the analytical instrument in an argon-filled vial. The data evaluation was carried out using the Netzsch Protens 4.0 program.

The elemental analyses were carried out by the microanalysis combustion methods using a Euro EA3000 from HEKA-Tech GmbH. The samples of air-sensitive substances were prepared in a dry box and transported to the analytical instrument in an argon-filled vial. The error limits for the recorded atoms are: C: ±0.3%, H: ±0.1%, N: ±0.2%.

EXAMPLE 1

Synthesis of $K[B(CN)_4]$

KCN, LiCl and $K[BF_4]$ are ground coarsely and mixed with one another in a mortar in a dry box (MBraun, Munich). The mixture is finely ground using a commercially available coffee grinder. The reaction mixture is subsequently transferred into a nickel crucible ($\varnothing_{internal}$=101 mm, $d_{wall}$=2 mm, h=85 mm). The crucible is covered loosely by an iron lid, transferred from the dry box into a muffle furnace (VMK 93, Kontron Material und Strukturanalyse GmbH) and heated. When the reaction is complete, the crucible with the metal cover is removed from the still-hot muffle furnace and cooled to room temperature in air.

The cooled grey/black porous reaction mixture is transferred out of the crucible into a mortar and crushed coarsely. 150 ml of water are subsequently added to the comminuted solid in a 3 l beaker, and a total of 350 ml of $H_2O_2$ (30% aqueous solution, about 3 mol) are added in approximately 30 ml portions over a period of half an hour with constant stirring. The reaction, which commences exothermically with vigorous evolution of gas, is controlled by addition of ice. The reaction mixture (V=2.3 l) is divided between two 3 l beakers and acidified using concentrated HCl (about 300 ml, about 3.6 mol) (pH 5-7) until gas evolution is no longer observed. It is subsequently checked whether cyanide residues are still present in the mixture (cyanide test, Merck KGaA, Darmstadt, Germany). The mixture is then filtered, and 28 ml (0.34 mol) of conc. HCl are added to the yellow solution with stirring. 47 g (63 ml, 0.33 mol) of tripropylamine are subsequently added. The reaction mixture is stirred for 15 minutes and extracted with dichloromethane (250, 150 and 50 ml). The combined organic phases are washed with 200 ml of $H_2O$, and the washings are re-extracted with 25 ml of dichloromethane. The combined dichloromethane phases are dried over $MgSO_4$ and filtered through a glass frit (D4). 35 g (0.63 mol) of KOH are dissolved in a little water and added to the organic solution with vigorous stirring. A beige oily substance immediately precipitates out and forms lumps on the vessel base after further stirring (30 min). The dichloromethane/tripropylamine mixture is decanted off, and the product is extracted from the residue with THF (200, 100 and 50 ml). The collected THF phases are dried using $K_2CO_3$, and finally all volatile constituents are removed in a rotary evaporator. The white product is washed with dichloromethane and dried at room temperature under reduced pressure.

TABLE 1

Synthesis of $K[B(CN)_4]$

| Temp. | Time | $K[BF_4]$ | | KCN | | LiCl | | $K[B(CN)_4]$ | | Yield |
| --- | --- | --- | --- | --- | --- | --- | --- | --- | --- | --- |
| ° C. | hrs | g | mol | G | mol | g | mol | g | mol | % |
| 300 | 1.5 | 37.2 | 0.30 | 170.3 | 2.62 | 116.1 | 2.74 | 29.2 [a] | 0.19 | 64 |
| 340 | 0.75 | 36.9 | 0.29 | 170.0 | 2.61 | 116.2 | 2.74 | 27.0 [a] | 0.18 | 60 |
| 340 | 1.25 | 36.9 | 0.29 | 169.9 | 2.61 | 115.9 | 2.74 | 26.7 [a] | 0.17 | 59 |
| 340 | 2 | 37.0 | 0.29 | 160.6 | 2.47 | 115.9 | 2.74 | 20.8 [a] | 0.14 | 46 |
| 340 | 3 | 36.7 | 0.29 | 172.5 | 2.65 | 102.8 | 2.42 | 20.3 [b] | 0.13 | 45 |
| 340 | 3 | 36.8 | 0.29 | 160.1 | 2.46 | 115.2 | 2.72 | 18.8 [a] | 0.12 | 42 |

TABLE 1-continued

Synthesis of K[B(CN)$_4$]

| Temp. | Time | K[BF$_4$] | | KCN | | LiCl | | K[B(CN)$_4$] | | Yield |
|---|---|---|---|---|---|---|---|---|---|---|
| °C. | hrs | g | mol | G | mol | g | mol | g | mol | % |
| 340 | 3 | 36.7 | 0.29 | 180.9 | 2.78 | 104.7 | 2.46 | 17.4 [a] | 0.11 | 39 |

[a] Oxidation of the unreacted CN⁻ using H$_2$O$_2$.
[b] Oxidation of the unreacted CN⁻ using NaOCl.

$^{13}$C{$^1$H}-NMR: δ=123.3 ppm (q, 4C, CN), $^1\Delta^{13}$C($^{10/11}$B)= 0.0021 ppm, $^1$J($^{11}$B,$^{13}$C)=70.9 Hz; $^{11}$B-NMR: δ=−38.6 ppm, $^1$J($^{11}$B,$^{13}$C)=71.2 Hz; solvent: CD$_3$CN reference substances: $^{13}$C-NMR solvent peak (against TMS) and $^{11}$B-NMR BF$_3$.Et$_2$O/CD$_3$CN as external standard.

The NMR data are identical with those in the prior art (E. Bernhardt, G. Henkel, H. Willner, Z. *Anorg. Allg. Chem.* 626 (2000) 560).

Results of the Elemental Analysis:

|  | C [%] | H [%] | N [%] |
|---|---|---|---|
| theoretical | 31.20 | — | 36.39 |
| found | 31.35 | — | 35.97 |

According to DSC measurements, the salt decomposes above 450° C.

EXAMPLE 2

Synthesis of Na[B(CN)$_4$]

170.3 g (2.62 mol) of KCN, 116.1 g (2.74 mol) of LiCl and 37.2 g (0.30 mol) of K[BF$_4$] are weighed out, ground coarsely in a mortar and mixed with one another. The further procedure corresponds to that described under Example 1 (reaction temperature 300° C., reaction time 1.5 hours) as far as the obtaining of the dichloromethane extract.

2 equivalents of NaOH (about 25 g, 0.63 mol) are dissolved in as little water as possible (about 10-20 ml) and added dropwise to the organic solution with vigorous stirring. A beige oily substance immediately precipitates out and forms lumps on the vessel base after further stirring (at least 30 min). The dichloromethane/tripropylamine mixture is decanted off, and the product is extracted from the residue with THF (200 ml, 100 ml and 50 ml). If the beige residue becomes liquid due to the extraction, its viscous consistency can be restored by careful addition of Na$_2$CO$_3$ or Na$_2$SO$_4$.

The collected THF phases are dried using Na$_2$CO$_3$ or Na$_2$SO$_4$, and finally all volatile constituents are removed in a rotary evaporator. The white product is washed with dichloromethane in order to remove amine residues and dried at 60° C. under reduced pressure. Yield 25.3 g (62%, 0.18 mol).

$^{13}$C{$^1$H}-NMR: δ=123.3 ppm (q, 4C, CN), $^1\Delta^{13}$C($^{10/11}$B)= 0.0021 ppm, $^1$J($^{11}$B,$^{13}$C)=70.9 Hz; $^{11}$B-NMR: δ=−38.6 ppm, $^1$J($^{11}$B,$^{13}$C)=71.2 Hz; solvent: CD$_3$CN reference substances: $^{13}$C-NMR solvent peak (against TMS) and $^{11}$B-NMR BF$_3$.Et$_2$O/CD$_3$CN as external standard The NMR data are identical with those in the prior art (E. Bernhardt, G. Henkel, H. Willner, Z. *Anorg. Allg. Chem.* 626 (2000) 560).

Results of the Elemental Analysis:

|  | C [%] | H [%] | N [%] |
|---|---|---|---|
| theoretical | 34.85 | — | 40.64 |
| found | 34.60 | — | 40.15 |

EXAMPLE 3

Lithium Tetracyanoborate, Li[B(CN)$_4$]

5 g (32 mmol) of K[B(CN)$_4$] are dissolved in 20 ml of water and reacted with 8 ml of 37% hydrochloric acid (96 mmol) and 8 ml of "Pr$_3$N (42 mmol). This mixture is then extracted twice with 50 ml of CH$_2$Cl$_2$ each time, the organic phase is dried using MgSO$_4$, and a solution of 3 g of LiOH.H$_2$O (72 mmol) in 20 ml of water is added, and the mixture is stirred vigorously for one hour. All volatile products are removed under reduced pressure. Li[B(CN)$_4$] is extracted from the residue with 50 ml of CH$_3$CN in a Soxlett apparatus. The organic phase is evaporated in a rotary evaporator. The crude product is recrystallised from water, washed with 50 ml of CH$_2$Cl$_2$ and freed from solvent residues under reduced pressure. Yield 3.5 g (80%, 29 mmol).

According to DSC measurements, the salt decomposes above 470° C.

EXAMPLE 4

Ammonium Tetracyanoborate, NH$_4$[B(CN)$_4$]

0.31 g (2.0 mmol) of K[B(CN)$_4$] are dissolved in 8 ml of water, then reacted with a solution of 0.20 g (1.1 mmol) of (NH$_4$)$_2$[SiF$_6$] in 8 ml of water. All volatile constituents are removed under reduced pressure. NH$_4$[B(CN)$_4$] is extracted from the residue with 10 ml of CH$_3$CN. The organic phase is evaporated in a rotary evaporator. The crude product is washed with 10 ml of CH$_2$Cl$_2$ and dried under reduced pressure. Yield 0.25 g (93%, 1.9 mmol).

According to DSC measurements, the salt decomposes above 300° C.

EXAMPLE 5

Trityl Tetracyanoborate, [Ph$_3$C][B(CN)$_4$]

500 mg (2.3 mmol) of Ag[B(CN)$_4$] and 726 mg (2.3 mmol) of (C$_6$H$_5$)$_3$CBr in anhydrous acetonitrile are brought to reaction in a 250 ml glass flask with PTFE valve (Young, London). The acetonitrile is removed under reduced pressure after 4 hrs, and 100 ml of dichloromethane are subsequently added. The suspension is filtered through a Celite®-covered frit in a Schlenk flask. The reaction flask is rinsed twice with dichloromethane (20 ml and 10 ml). The solution is evaporated to 10 ml under reduced pressure, and, after addition of 70 ml of anhydrous hexane, an orange solid precipitates out. This is filtered off via a Schlenk frit and rinsed with a further 10 ml of hexane. The orange [$Ph_3C$][$B(CN)_4$] is dried under reduced pressure and stored in a dry box. The yield is 408 mg (51%, 1.3 mmol).

$^1$H-NMR: δ=7.73 ppm (m, 6H, o-H), δ=7.94 ppm (m, 6H, m-H), δ=8.31 ppm (tt, 3H, p-H); $^{13}$C{$^1$H}-NMR: δ=122.7 ppm (q, 4C, CN), $^1$J($^{11}$B,$^{13}$C)=71.5 Hz, δ=131.0 ppm (s, 6C, m-C), δ=140.2 ppm (s, 3C, i-C), δ=143.0 ppm (s, 6C, o-C), δ=143.8 ppm (s, 3C, p-C), δ=211.2 ppm (s, 1C, C$^+$); $^{11}$B-NMR: δ=−38.6 ppm, $^1$J($^{11}$B,$^{13}$C)=71.3 Hz; solvent: CDCl$_3$ reference substances: $^1$H- and $^{13}$C-NMR solvent signal (against TMS) and $^{11}$B-NMR BF$_3$.Et$_2$O/CD$_3$CN as external standard Results of the Elemental Analysis [$Ph_3C$][$B(CN)_4$]:

|  | C [%] | H [%] | N [%] |
|---|---|---|---|
| theoretical | 77.12 | 4.22 | 15.64 |
| found | 77.19 | 4.21 | 15.50 |

[$Ph_3C$][$B(CN)_4$] melts at 158° C. with decomposition.

EXAMPLE 6

[$HNPhMe_2$][$B(CN)_4$]

1.50 g (9.7 mmol) of K[$B(CN)_4$] are dissolved in 50 ml of water. Firstly 3 ml (36 mmol) of conc. HCl solution and subsequently 1.23 ml (9.7 mmol) of N,N-di-methylaniline are added to the solution with stirring, whereupon a white solid precipitates out. The solution is extracted twice with dichloromethane (100 ml and 30 ml), the organic phase is dried using MgSO$_4$, and the dichloromethane is removed under reduced pressure, giving white [$HNPhMe_2$][$B(CN)_4$], which is purified by washing with pentane. Yield 2.12 g (92%, 8.9 mmol).

$^1$H-NMR: δ=3.23 ppm (s, 6H, CH$_3$), $^1$Δ$^1$H($^{12/13}$C)=−0.0023, $^1$J($^1$H, $^{13}$C)−145.48 Hz, δ=7.64-7.58 ppm (m, 5H, C$_6$H$_5$); $^{13}$C{$^1$H}-NMR: δ=47.8 ppm (s, 2C, CH$_3$), δ=121.5 ppm (s, 2C, C$_6$H$_5$), δ=123.2 ppm (s, 4C, CN), $^1$J($^{11}$B,$^{13}$C)= 71.3 Hz, $^1$Δ$^{13}$C($^{10/11}$B)=−0.0020 ppm, δ=131.5 ppm (s, 2C, C$_6$H$_5$), δ=131.6 ppm (s, 1C, C$_6$H$_5$), δ=143.1 ppm (s, 1C, C$_6$H$_5$); $^{11}$B-NMR: δ=−38.6 ppm, $^1$J($^{11}$B,$^{13}$C)=71.3 Hz; $^{15}$N-NMR: δ=−103.2 ppm (q, 4N, CN), $^1$J($^{11}$B,$^{15}$N)=0.73 Hz; solvent: CD$_3$CN; reference substances: $^1$H- and $^{13}$C-NMR solvent signal (against TMS), $^{11}$B-NMR BF$_3$.Et$_2$O/CD$_3$CN as external standard and $^{15}$N-NMR 80% of CH$_3$NO$_2$ in CD$_3$CN as external standard.

Results of the Elemental Analysis of [$HNPhMe_2$][$B(CN)_4$]:

|  | C [%] | H [%] | N [%] |
|---|---|---|---|
| theoretical | 60.80 | 5.10 | 29.54 |
| found | 60.60 | 4.65 | 28.50 |

[$HNPhMe_2$][$B(CN)_4$] melts at 101° C. and decomposes exothermically above 246° C.

EXAMPLE 7

Tetraethylammonium Tetracyanoborate, [$E4N$][$B(CN)_4$]

7 g (46 mmol) of K[$B(CN)_4$] are dissolved in 300 ml of water and 8.4 g (46 mmol) of [$Et_4N$]Cl.H$_2$O are dissolved in 130 ml of water. The two solutions are combined, whereupon a white solid precipitates oit. After stirring for 30 minutes, 250 ml of dichloromethane in which the precipitated substance dissolves are added. The two phases are separated, and the organic phase is dried over MgSO$_4$. The dichloromethane is removed in a rotary evaporator, and the white solid is washed a number of times with pentane and subsequently dried under reduced pressure. Yield 10.5 g (96%, 43 mmol).

$^1$H-NMR: δ=1.22 ppm (tt, 12H, CH$_3$), $^1$Δ$^1$H($^{12/13}$C)=−0.0019 ppm, $^1$J(1H,$^{13}$C)=128.78 Hz, $^3$J(1H$^1$,$^1$H)=7.27 Hz; δ=3.13 ppm (q, 8H, CH$_2$), $^1$Δ$^1$H($^{12/13}$C)=0.0034 ppm, $^1$J($^1$H, $^{13}$C)=144.30 Hz, $^2$J($^1$H,$^{14}$N)=1.89 Hz, $^3$J($^1$H,$^1$H)=7.28 Hz; $^{13}$C{$^1$H}-NMR: δ=7.8 ppm (s, 4C, CH$_3$); δ=53.2 ppm (t, 4C, CH$_2$), $^1$J($^{13}$C,$^{15}$N)=3.1 Hz; δ=123.3 ppm (q, 4C, CN), $^1$Δ$^{13}$C($^{10/11}$B)=0.0021 ppm, $^1$J($^{11}$B,$^{13}$C)=70.9 Hz; $^{11}$B-NMR: δ=−38.6 ppm, $^1$J($^{11}$B,$^{13}$C)=71.2 Hz; solvent: CD$_3$CN reference substances: $^1$H- and $^{13}$C-NMR solvent peak (against TMS) and $^{11}$B-NMR BF$_3$.Et$_2$O/CD$_3$CN as external standard.

Results of the Elemental Analysis of [$E4N$][$B(CN)_4$]:

|  | C [%] | H [%] | N [%] |
|---|---|---|---|
| theoretical | 58.8 | 8.22 | 28.57 |
| found | 58.5 | 8.18 | 28.22 |

[$E4N$][$B(CN)_4$] melts at 230° C. A further reversible phase conversion occurs at a temperature of 145° C. The salt decomposes above 360° C.

EXAMPLE 8

1-Butyl-3-methylimidazolium Tetracyanoborate [$C_8H_{15}N_2$][$B(CN)_4$]

0.35 g (2.3 mmol) of K[$B(CN)_4$] are dissolved in 20 ml of water. 0.53 g (3.0 mmol) of [$C_8H_{15}N_2$]Cl in 20 ml of water are added with stirring. The solution is extracted twice with dichloromethane (30 ml and 20 ml), the organic phase is washed with water (20 ml) and dried using MgSO$_4$, and the dichloromethane is subsequently removed under reduced pressure. Yield 0.50 g (87%, 2.0 mmol).

Results of the Elemental Analysis of [$C_8H_{15}N_2$][$B(CN)_4$]:

|  | C [%] | H [%] | N [%] |
|---|---|---|---|
| theoretical | 56.70 | 5.95 | 33.07 |
| found | 56.24 | 6.13 | 32.99 |

$[C_8H_{15}N_2][B(CN)_4]$ melts below −50° C. and decomposes endothermically above 410° C.

EXAMPLE 9

1-Ethyl-3-methylimidazolium Tetracyanoborate $[C_6H_{11}N_2][B(CN)_4]$ $[C_6H_{11}N_2][B(CN)_4]$ is prepared analogously to $[C_8H_{15}N_2][B(CN)_4]$ with the same yield.

Results of the Elemental Analysis of $[C_6H_{11}N_2][B(CN)_4]$:

|  | C [%] | H [%] | N [%] |
| --- | --- | --- | --- |
| theoretical | 53.13 | 4.90 | 37.18 |
| found | 52.79 | 4.97 | 37.12 |

$[C_6H_{11}N_2][B(CN)_4]$ melts below −50° C. and decomposes endothermically above 420° C.

EXAMPLE 10 p-Methylbutylpyridinium Tetracyanoborate $[C_{10}H_{16}N][B(CN)_4]$ $[C_{10}H_{16}N][B(CN)_4]$ is prepared analogously to $[C_8H_{15}N_2][B(CN)_4]$ with the same yield.

Results of the Elemental Analysis of $[C_{10}H_{16}N][B(CN)_4]$:

|  | C [%] | H [%] | N [%] |
| --- | --- | --- | --- |
| theoretical | 63.42 | 6.08 | 26.42 |
| found | 62.81 | 6.13 | 26.70 |

$[C_{10}H_{16}N][B(CN)_4]$ solidifies at −25° C., melts at 42° C. and decomposes endothermically above 390° C.

EXAMPLE 11

Preparation of $K[BF_2(CN)_2]$

Variant A: 5.88 g (41 mmol) of $BF_3 \cdot OEt_2$ and 30 ml of $CH_3CN$ are condensed onto 4.12 g (63 mmol) of KCN in a 50 ml flask with PTFE valve. The reaction mixture is stirred at room temperature for 3 h, and all volatile constituents are subsequently removed under reduced pressure, and the residue is dissolved in about 50 ml of $CH_3CN$ and freed from KCN and $K[BF_4]$ by filtration. After removal of the acetonitrile under reduced pressure, 2.66 g (19 mmol) of $K[BF_2(CN)_2]$ ($^{11}$B- and $^{19}$F-NMR: 93% of $[BF_2(CN)_2]^−$, 0.3% of $[BF_3(CN)]^−$ and about 7% of unknown species) are obtained. Yield: 92%. Pure colourless $K[BF_2(CN)_2]$ is obtained by recrystallisation from water. Isolated yield: 2.08 g (72%, 15 mmol).

Variant B: 65 g (1.0 mol) of KCN and 200 ml of $CH_3CN$ are initially introduced in a 500 ml round-bottomed flask with dropping funnel. 50 ml (56 g, 0.4 mol) of $BF_3 \cdot OEt_2$ are added dropwise over the course of half an hour with stirring at room temperature. During the addition, the temperature rises to 50° C. After further stirring (1.5 h) at room temperature, the solution is filtered off, and the filter residue (KCN and $K[BF_4]$) is washed with about 300 ml of $CH_3CN$. The combined acetonitrile phases are evaporated in a rotary evaporator, giving 20 g of impure $K[BF_2(CN)_2]$ as crude product. The crude product is reacted with 30 ml of conc. HCl and 35 ml (25 g, 170 mmol) of tripropylamine in 200 ml of water and extracted as tripropylammonium salt with 200 ml of dichloromethane. The dichloromethane phase is dried using $MgSO_4$ and reacted with vigorous stirring with 25 g of KOH dissolved in as little water as possible. The viscous aqueous phase is separated off and washed with dichloromethane. The product is extracted from the residue with about 300 ml of $CH_3CN$, and the solution is dried using $K_2CO_3$ and evaporated in a rotary evaporator. The white product is washed with dichloromethane and dried under reduced pressure. Yield: 17 g (60%, 120 mmol). According to $^{11}$B-NMR, the substance contains 98% of $[BF_2(CN)_2]^−$.

EXAMPLE 12

1-Ethyl-3-methylimidazolium Tricyanofluoroborate $[C_6H_{11}N_2][BF(CN)_3]$ $[C_6H_{11}N_2][BF(CN)_3]$ is prepared analogously to $[C_8H_{15}N_2][B(CN)_4]$ with yield.

Results of the Elemental Analysis of $[C_6H_{11}N_2][BF(CN)_3]$:

|  | C [%] | H [%] | N [%] |
| --- | --- | --- | --- |
| theoretical | 49.35 | 5.06 | 31.98 |
| found | 48.52 | 4.84 | 31.20 |

$[C_6H_{11}N_2][BF(CN)_3]$ is liquid at room temperature.

EXAMPLE 13

1-Butyl-3-methylimidazolium Tricyanofluoroborate $[C_8H_{15}N_2][BF(CN)_3]$ $[C_8H_{15}N_2][BF(CN)_3]$ is prepared analogously to $[C_8H_{15}N_2][B(CN)_4]$ yield.

Results of the Elemental Analysis of $[C_8H_{15}N_2][BF(CN)_3]$:

|  | C [%] | H [%] | N [%] |
| --- | --- | --- | --- |
| theoretical | 53.47 | 6.12 | 28.34 |
| found | 54.06 | 6.09 | 28.68 |

$[C_8H_{15}N_2][BF(CN)_3]$ melts below −50° C. and decomposes exothermically above 300° C.

EXAMPLE 14 p-Methylbutylpyridinium Tricyanofluoroborate $[C_{10}H_{16}N][BF(CN)_3]$ $[C_{10}H_{16}N][BF(CN)_3]$ is prepared analogously to $[C_8H_{15}N_2][B(CN)_4]$ with the same yield.

Results of the Elemental Analysis of $[C_{10}H_{16}N][BF(CN)_3]$:

|  | C [%] | H [%] | N [%] |
| --- | --- | --- | --- |
| theoretical | 60.50 | 6.25 | 21.71 |
| found | 61.13 | 5.51 | 22.35 |

$[C_{10}H_{16}N][BF(CN)_3]$ melts below −50° C. and decomposes exothermically above 260° C.

EXAMPLE 15

1-Ethyl-3-methylimidazolium Dicyanodifluoroborate $[C_6H_{11}N_2][BF_2(CN)_2]$ $[C_6H_{11}N_2][BF_2(CN)_2]$ is prepared analogously to $[C_8H_{15}N_2][B(CN)_4]$ with the same yield.

Results of the Elemental Analysis of $[C_6H_{11}N_2][BF_2(CN)_2]$:

|  | C [%] | H [%] | N [%] |
|---|---|---|---|
| theoretical | 45.32 | 5.23 | 26.43 |
| found | 45.14 | 5.14 | 26.28 |

$[C_6H_{11}N_2][BF_2(CN)_2]$ melts below −50° C. and decomposes exothermically above 200° C.

EXAMPLE 16

1-Butyl-3-methylimidazolium Dicyanodifluoroborate $[C_8H_{15}N_2][BF_2(CN)_2]$ $[C_8H_{15}N_2][BF_2(CN)_2]$ is prepared analogously to $[C_8H_{15}N_2][B(CN)_4]$ with the same yield.

Results of the Elemental Analysis of $[C_8H_{15}N_2][BF_2(CN)_2]$:

|  | C [%] | H [%] | N [%] |
|---|---|---|---|
| theoretical | 50.03 | 6.30 | 23.34 |
| found | 50.20 | 6.31 | 23.42 |

$[C_8H_{15}N_2][BF_2(CN)_2]$ melts below −50° C. and decomposes exothermically above 210° C.

EXAMPLE 17 p-Methylbutylpyridinium Dicyanodifluoroborate $[C_{10}H_{16}N][BF_2(CN)_2]$ $[C_{10}H_{16}N][BF_2(CN)_2]$ is prepared analogously to $[C_8H_{15}N_2][B(CN)_4]$ with the same yield.

Results of the Elemental Analysis of $[C_{10}H_{16}N][BF_2(CN)_2]$:

|  | C [%] | H [%] | N [%] |
|---|---|---|---|
| theoretical | 57.40 | 6.42 | 16.74 |
| found | 57.70 | 6.20 | 16.95 |

$[C_{10}H_{16}N][BF_2(CN)_2]$ melts below −50° C. and decomposes exothermically above 190° C.

We claim:

1. A process for the preparation of alkali metal cyanoborates of formula (1)

$$M^+[B(CN)_4]^- \qquad (1),$$

where M is Li, Na, K, Rb or Cs,
comprising reacting an alkali metal tetrafluoroborate $M[BF_4]$, where M=Li, Na, K, Rb or Cs with an alkali metal cyanide MCN, where M=Li, Na, K, Rb, or Cs, in a solid-state reaction.

2. The process according to claim 1, wherein the alkali metal tetrafluoroborate is $K[BF_4]$ or $Na[BF_4]$, and in that the alkali metal cyanide is KCN or NaCN.

3. The process according to claim 1, comprising reacting the alkali metal tetrafluoroborate with the alkali metal cyanide in the presence of a lithium halide which is LiCl, LiBr or LiI.

4. The process according to claim 3, wherein the alkali metal cyanide and the lithium halide are employed in the molar ratio 1:1.

5. The process according to claim 1, wherein the alkali metal tetrafluoroborate and the alkali metal cyanide are employed in the molar ratio of 1:4 to 1:12.

6. The process according to claim 1, wherein the alkali metal tetrafluoroborate employed is $K[BF_4]$ and the alkali metal cyanide employed is KCN.

7. The process according to claim 1, wherein reacting is carried out at temperatures between 100° C. and 500° C.

8. A process for the preparation of alkali metal cyanoborates of formula (2)

$$M^+[BF_n(CN)_{4-n}]^- \qquad (2),$$

where n=0, 1, 2 or 3
and M is Li, Na, K, Rb or Cs,
comprising reacting an alkali metal cyanide MCN with boron trifluoride etherate $BF_3OEt_2$.

9. The process according to claim 8, comprising reacting the alkali metal cyanide with the boron trifluoride etherate in the presence of an aprotic solvent.

10. The process according to claim 9, comprising reacting the alkali metal cyanide with the boron trifluoride etherate in the presence of acetonitrile, diethyl ether, tetrahydrofuran and/or dimethoxyethane.

11. The process according to claim 8, wherein the alkali metal cyanide is potassium cyanide KCN.

12. The process according to claim 8, wherein the reaction is carried out at temperatures of −80 to 100° C.

13. A process for the preparation of a salt of formula (3)

$$Kt^+[BF_n(CN)_{4-n}]^- \qquad (3),$$

where n=0, 1, 2 or 3, and $Kt^+$ is an organic cation, with the proviso that the cation $Kt^+$ is not $[N(C_4H_9)_4]^+$ for n=0,
comprising reacting an alkali metal cyanoborate of formula $M^+[B(CN)_4]^-$, where M is Li, Na, K, Rb or Cs, prepared according to claim 1 with $Kt^+X^-$,
where X is Cl, Br or I, and $Kt^+$ is an organic cation, with the proviso that the cation $Kt^+$ is not $[N(C_4H_9)_4]^+$ for n=0.

14. The process according to claim 13, wherein the organic cation $Kt^+$ is

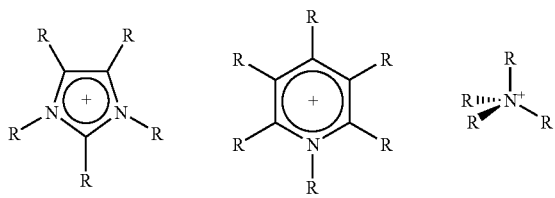

-continued

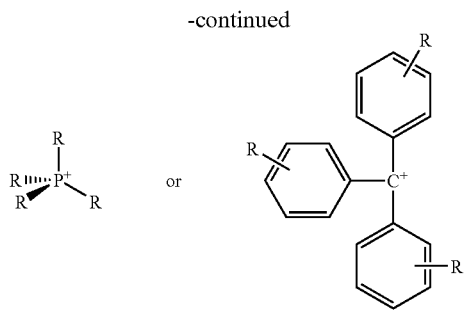

where R=H, with the proviso that at least one R on the nitrogen or phosphorous atom is different from H, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, with the proviso that no halogen-hetero atom bond is present, —$NO_2$, with the proviso that no bond to a positively charged hetero atom is present, and at least one R is different from $NO_2$, —CN, with the proviso that no bond to a positively charged hetero atom is present, and at least one R is different from CN, where the R are in each case identical or different, where the R may be bonded to one another in pairs by single or double bond, where one or more R may be partially or fully substituted by halogens, or partially by —CN or —$NO_2$, with the proviso that not all R are fully halogenated, and where one or two carbon atoms of the R may be replaced by hetero atoms and/or —O—, —C(O)—, C(O)O—, —S—, —S(O)—, —$SO_2$—, —$S(O)_2$O—, —N=, —P=, —NR'—, —PR'—, —P(O)(OR')—, —P(O)(OR')O—, —P(O)(NR'R')—, —P(O)(NR'R')O—, —P(O)(NR'R')NR'—, —S(O)NR'— or —$S(O)_2$NR'—, where R'=H, non-, partially or perfluorinated $C_1$- to $C_6$-alkyl or non-, partially or perfluorinated phenyl.

15. The process according to claim 13, wherein the organic cation $Kt^+$ is

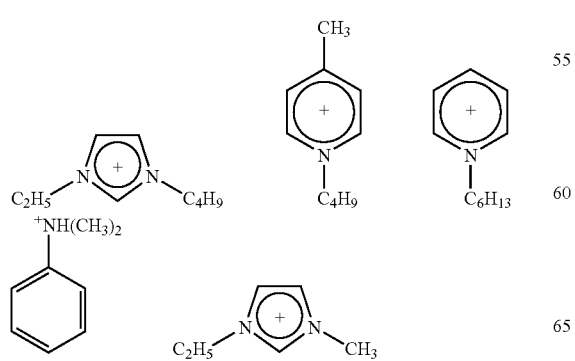

-continued

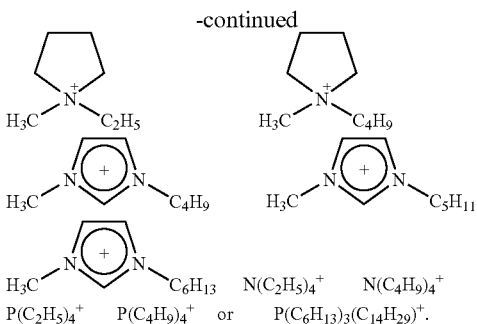

16. A salt of formula (3)

$$Kt^+[BF_n(CN)_{4-n}]^-  \qquad (3)$$

where n=1, 2 or 3, and $Kt^+$ is an organic cation.

17. The salt according to claim 16, wherein the organic cation $Kt^+$ is

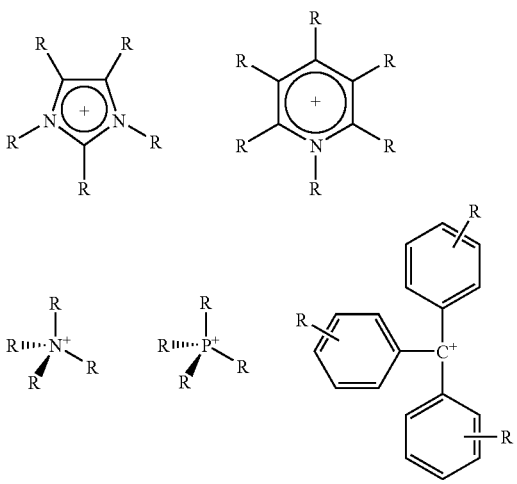

where R=H, with the proviso that at least one R on the N or P atom is different from H, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, with the proviso that no halogen-hetero atom bond is present, —$NO_2$, with the proviso that no bond to a positively charged hetero atom is present, and at least one R is different from $NO_2$, —CN, with the proviso that no bond to a positively charged hetero atom is present, and at least one R is different from CN, where the R are in each case identical or different, where the R may be bonded to one another in pairs by single or double bond, where one or more R may be partially or fully substituted by halogens, or partially by —CN or —$NO_2$, with the proviso that not all R are fully halogenated, and where one or two carbon atoms of the R may be replaced by hetero atoms and/or —O—, —C(O)—, C(O)O—, —S—, —S(O)—, —SO$_2$—, —S(O)$_2$O—, —N=, —P=, —NR'—, —PR'—, —P(O)(OR')—, —P(O)(OR')O—, —P(O)(NR'R')—, —P(O)(NR'R')O—, —P(O)(NR'R')NR'—, —S(O)NR'— and —S(O)$_2$NR'—, where R'=H, non-, partially or perfluorinated C$_1$- to C$_6$-alkyl or non-, partially or perfluorinated phenyl.

18. The salt according to claim 16, wherein the organic cation Kt$^+$ is

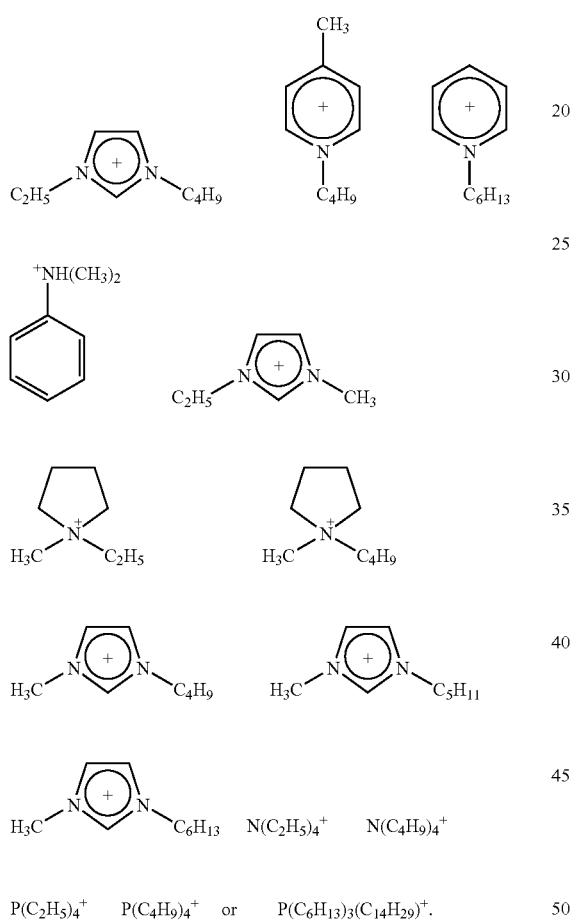

19. A process for the preparation of a salt of formula (3)

$$Kt^+[BF_n(CN)_{4-n}]^- \quad (3),$$

where n=0, 1, 2 or 3, and Kt$^+$ is an organic cation, with the proviso that the cation Kt$^+$ is not [N(C$_4$H$_9$)$_4$]$^+$ for n=0, comprising reacting an alkali metal cyanoborate of formula M[BF$_n$(CN)$_{4-n}$]$^-$, where n=0, 1, 2 or 3 and M is Li, Na, K, Rb or Cs, prepared according to claim 8, with Kt$^+$X$^-$, where X is Cl, Br or I, and Kt$^+$ is an organic cation, with the proviso that the cation Kt$^+$ is not [N(C$_4$H$_9$)$_4$]$^+$ for n=0.

20. A salt of the following formula

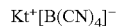

where Kt$^+$ is an organic cation of one of the following formulae

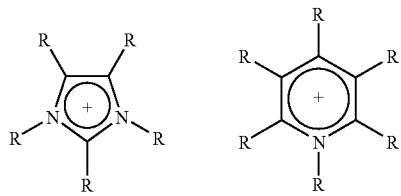

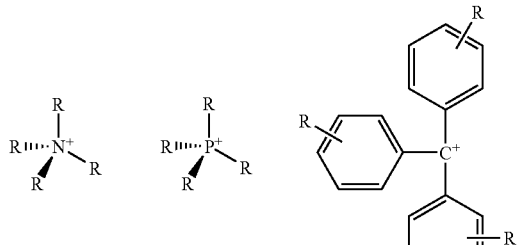

where R=H, with the proviso that at least one R on the N or P atom is different from H, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, with the proviso that no halogen-hetero atom bond is present, —NO$_2$, with the proviso that no bond to a positively charged hetero atom is present, and at least one R is different from NO$_2$, —CN, with the proviso that no bond to a positively charged hetero atom is present, and at least one R is different from CN, where the R are in each case identical or different, where the R may be bonded to one another in pairs by single or double bond, where one or more R may be partially or fully substituted by halogens, or partially by —CN or —NO$_2$, with the proviso that not all R are fully halogenated, and where one or two carbon atoms of the R may be replaced by hetero atoms and/or —O—,

—C(O)O—, —S—, —S(O)$_2$O—, —N=, —P=, —NR'—, —P(O)(OR')—,

—P(O)(OR')O—, —P(O)(NR'R')—,

—P(O)(NR'R')O—, —P(O)(NR'R')NR'—, —S(O)NR'— and —S(O)$_2$NR'—, where R'=H, non-, partially or perfluorinated C$_1$- to C$_6$-alkyl or non-, partially or perfluorinated phenyl, with the proviso that the cation Kt$^+$ is not [N(C$_4$H$_9$)$_4$]$^+$.

21. A salt according to claim 20, wherein $Kt^+$ is a cation of the following formula
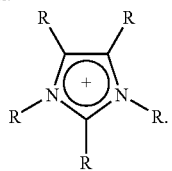
22. A salt according to claim 20, wherein $Kt^+$ is a cation of the following formula
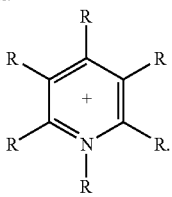
23. A salt according to claim 20, wherein $Kt^+$ is a cation of one of the following formulae
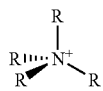  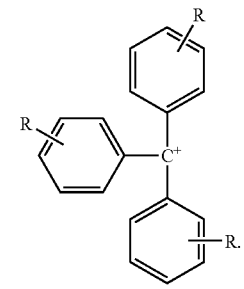
* * * * *

UNITED STATES PATENT AND TRADEMARK OFFICE
CERTIFICATE OF CORRECTION

PATENT NO.        : 7,645,434 B2                                              Page 1 of 1
APPLICATION NO.   : 10/545690
DATED             : January 12, 2010
INVENTOR(S)       : Welz-Biermann et al.

It is certified that error appears in the above-identified patent and that said Letters Patent is hereby corrected as shown below:

Column 19, line 62 reads "mula M[BF$_n$(CN)$_{4-n}$]$^-$, where n-0, 1, 2 or 3 and M is Li," should read -- mula M$^+$[BF$_n$(CN)$_{4-n}$]$^-$, where n-0, 1, 2 or 3 and M is Li, --.

Column 20, line 59 reads "-C(O)O-, -S-, -S(O)$_2$O-, -N=, -P=," should read -- -C(O)-, C(O)O-, -S-, -S(O)-, -SO$_2$-, -S(O)$_2$O-, -N=, -P=, --.

Column 20, line 60, reads "-NR'-, -P(O)(OR')-," should read -- -NR'-, -PR'-, -P(O)(OR')-, --.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,645,434 B2 |
| APPLICATION NO. | : 10/545690 |
| DATED | : January 12, 2010 |
| INVENTOR(S) | : Welz-Biermann et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1126 days.

Signed and Sealed this

Sixteenth Day of November, 2010

David J. Kappos
*Director of the United States Patent and Trademark Office*